United States Patent [19]

de Haan et al.

[11] 4,109,022

[45] Aug. 22, 1978

[54] FLAVORING WITH TRANS, E-1-CROTONOYL-2,2,6-TRIMETHYLCY-CLOHEXANE

[75] Inventors: Douwe Rienk de Haan, Soest; Dirk Karel Kettenes, Putten, both of Netherlands

[73] Assignee: P.F.W. Beheer B.V., Amersfoort, Netherlands

[21] Appl. No.: 681,202

[22] Filed: Apr. 28, 1976

[30] Foreign Application Priority Data

Oct. 26, 1972 [GB] United Kingdom ............... 49368/72

[51] Int. Cl.$^2$ ............................................ A23L 1/235

[52] U.S. Cl. .................................................. 426/538

[58] Field of Search ........................................ 426/538

[56] References Cited

U.S. PATENT DOCUMENTS

| | | | |
|---|---|---|---|
| 3,890,370 | 6/1975 | Buchi et al. | 426/538 X |
| 3,892,809 | 7/1975 | Schulte-Elte | 426/538 X |
| 3,928,456 | 12/1975 | Kovats et al. | 426/538 X |
| 3,956,392 | 5/1976 | de Haan et al. | 426/538 X |

*Primary Examiner*—Joseph M. Golian
*Attorney, Agent, or Firm*—Finnegan, Henderson, Farabow & Garrett

[57] ABSTRACT

1-Crotonoyl-2,2,6-trimethylcyclohexane occurs in four stereoisomeric forms. In particular the trans, E isomer has interesting organoleptic properties and is useful in the preparation of perfume and flavoring compositions. Processes for preparing the stereoisomers, in a pure form or as mixtures, are described.

8 Claims, 2 Drawing Figures

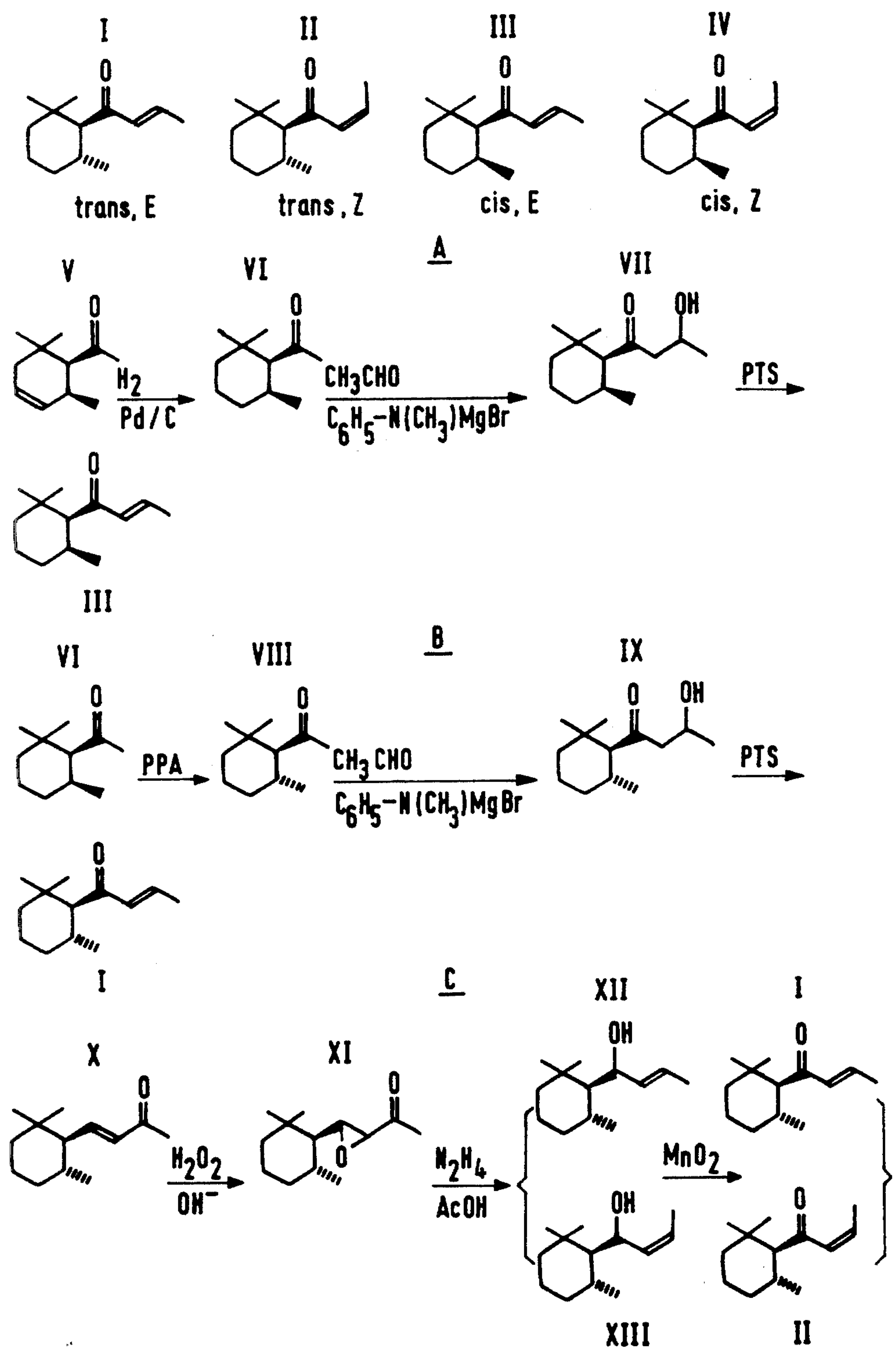
I
II
III
IV
trans, E
trans, Z
cis, E
cis, Z
A
V
VI
VII
H2
Pd/C
CH3CHO
C6H5-N(CH3)MgBr
PTS
III
B
VI
VIII
IX
PPA
CH3CHO
C6H5-N(CH3)MgBr
I
C
X
XI
XII
I
H2O2
OH-
N2H4
AcOH
MnO2
XIII
II

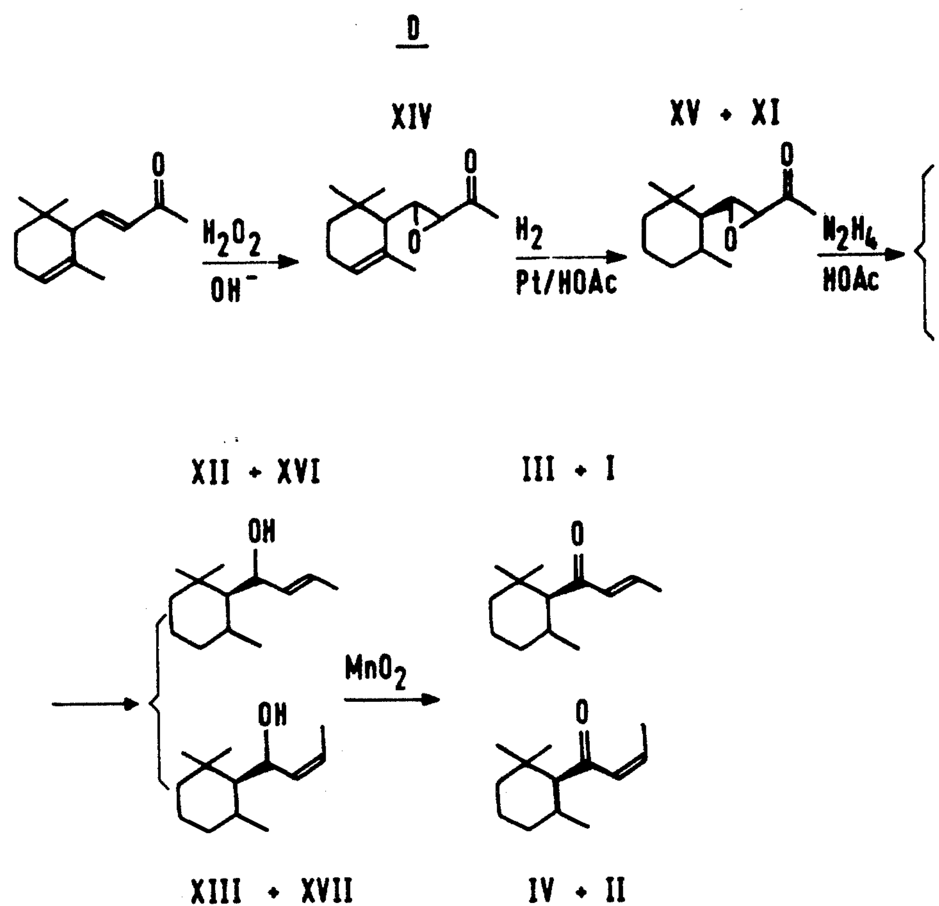
D
XIV
XV + XI
O
$H_2O_2$
$OH^-$
$H_2$
Pt/HOAc
$N_2H_4$
HOAc
XII + XVI
III + I
OH
$MnO_2$
XIII + XVII
IV + II

FLAVORING WITH TRANS, E-1-CROTONOYL-2,2,6-TRIMETHYLCYCLOHEXANE

This is a division of application Ser. No. 409,099, filed Oct. 24, 1973, now U.S. Pat. No. 3,956,392.

The present invention relates to the four stereoisomers of 1-crotonoyl-2,2,6-trimethylcyclohexane, more particularly to the trans, E isomer, which possesses unexpected interesting organoleptic properties and which therefore is useful in the preparation of a great variety of perfume and flavouring compositions.

Although many examples of crotonoyl-trimethylcyclohexenes and cyclohexadienes are known as flavouring and perfume materials in the recent patent literature (as are the methods of their preparation), (e.g. Dutch patent application No. 70,06649; Dutch patent application No. 68,15985; British Patent No. 1,240,309; Swiss Patent No. 509,399; Swiss Patent No. 521,099; Swiss Patent No. 521,298; E. Demole et al., Helv. Chim. Acta 53, 541 (1970), surprisingly enough there is no mention in the prior art of analogous compounds with a saturated ring system. Careful testing of the four stereoisomers has shown them to be not only totally different from the compounds with an unsaturated ring system but also strikingly different from each other. This is less surprising than it may seem at first glance; it is known to anybody skilled in the art that the effect on the olfactive properties, as a consequence of hydrogenation of a double bond or differences in the stereochemistry of a molecule, cannot be predicted.

The trans, E isomer is fresh fruity an devoid of any woody and β-ionone character, which as a rule is observed in the afore-mentioned compounds with an unsaturated ring system. Moreover the trans, E isomer has been found to be superior to both the latter compounds and to its stereoisomers in all flavour and perfume applications tested.

The four possible stereoisomers of the compound of this invention, represented by formulas I – IV, can be prepared in a pure form or as mixtures by known per se methods.

An example of the preparation of III is the hydrogenation of cis-1-acetyl-2,2,6-trimethyl-4-cyclohexene (V). The resulting cis-1-acetyl-2,2,6-trimethylcyclohexane (VI) is condensed with acetaldehyde and the obtained aldol product VII is dehydrated to III. This synthesis can be illustrated by reaction scheme A. The hydrogenation of V can be performed in alcoholic solution with 10% palladium on charcoal as a catalyst. The resulting saturated ketone VI is then condensed with acetaldehyde under influence of N-methylanilinomagnesium bromide as described by A. T. Nielsen et al in J.Am.Chem.Soc. 73, 4696 (1951). The aldol product VII is subsequently dehydrated in, for example, boiling methylene chloride or (azeotropically) in boiling benzene, both under the influence of p-toluenesulphonic acid to cis, E-1-crotonoyl-2,2,6-trimethyl-cyclohexane (III).

An example of the preparation of I is the epimerization of cis-1-acetyl-2,2,6-trimethylcyclohexane (VI) to the trans isomer VIII, which is condensed with acetaldehyde to the aldol product IX, and then dehydrated to I. This synthesis can be illustrated by reaction scheme B. Cis-1-Acetyl-2,2,6-trimethylcyclohexane (VI) can be epimerized by polyphosphoric acid at elevated temperatures. The condensation step and the dehydration are performed in the same way as described for the cis isomer III.

The starting material cis-1-acetyl-2,2,6-trimethyl-4-cyclohexene (V) can be prepared by the method described by K. S. Ayyar et al in Chem.Comm. 1973, 161 from 1,3-pentadiene and mesityl oxide in a Diels Alder-type reaction catalyzed by aluminum chloride.

An example of the preparation of a 70 : 30 mixture of I + II is the epoxidation of trans-dihydroionone (X), after which the resulting epoxide (XI) is converted by a Wharton reaction into a mixture of the unsaturated alcohols (XII and XIII), which are oxidized to a mixture of the corresponding ketones I + II. This synthesis can be illustrated by reaction scheme C. Trans-Dihydroionone (X) is epoxidized at 40° C with an alkaline solution of 30% hydrogen peroxide. The obtained epoxide (XI) is rearranged by the addition of hydrazine hydrate and acetic acid in methanolic solution at room temperature. The subsequent-oxidation of the formed mixture of unsaturated alcohols XII and XIII, yielding trans, E-1-crotonoyl-2,2,6-trimethylcyclohexane (I, 70%) and trans, Z-1-crotonoyl-2,2,6-trimethylcyclohexane (II, 30%) can be performed in several ways. A satisfactory method is the oxidation with manganese dioxide in an inert solvent such as pentane. On standing II isomerizes to I. The starting material trans-dihydroionone (X) can be prepared by known methods, such as the condensation of dihydrocyclocitral with acetone under basic conditions (V. Prelog and H. Frick, Helv.-Chim. Acta 31, 417 (1948); M. de Botton, Bull.Soc.-Chim.France 1966, 2212, 2466).

A further example of the preparation of a mixture of all four stereoisomers is the epoxidation of α-ionone, after which the resulting epoxide XIV is hydrogenated to a mixture of dihydroionone epoxides XV and XI. These are converted by a Wharton-reaction into a mixture of the unsaturated alcohols XII, XIII, XVI and XVII, which are oxidized to a mixture of the corresponding ketones. This synthesis can be illustrated by reaction scheme D. α-Ionone is epoxidized at 40° C with an alkaline solution of 30% hydrogen peroxide. The obtained epoxide XIV is hydrogenated in acetic acid solution with platinum as the catalyst to the dihydroionone epoxides XV and XI, which are rearranged by addition of hydrazine hydrate and acetic acid in methanolic solution at room temperature. The subsequent oxidation of the formed mixture of the unsaturated alcohols XII, XIII, XVI and XVII, yielding a mixture of the four possible stereoisomers I, II, III, and IV respectively, of 1-crotonoyl-2,2,6-trimethylcyclohexane, can be performed in several ways. A satisfactory method is the oxidation with manganese dioxide in an inert solvent as for example pentane. The Z isomers II and IV have each been isolated in pure form by preparative vapour phase chromatography.

The trans, E-1-crotonoyl-2,2,6-trimethylcyclohexane possesses a powerful odour that can be described as very natural fruity, rich and warm, with an earthy-minty shading that accentuates the natural character. Its tenacity, when smelled on evaporation-blotterstrips, is very good and makes this compound of great interest for use in compositions of floral and/or woody character like iris, mimosa, boronia, tobacco, and fancy bouquets.

Use levels in floral compositions may vary within a wide range, preferably between 0.05% and 5%, whereas in compositions with a tobacco leaf or a rose leaf character the level may be considerably higher. In flavour compositions, use levels may vary within a wide range as well; in either case the powerful flavour of trans, E-1-crotonoyl-2,2,6-trimethylcyclohexane is obvious. In flavouring compositions the percentage of trans, E-1-crotonoyl-2,2,6-trimethylcyclohexane can be varied between 0.001% and 1% of the flavouring composition, depending on the choice of the other ingredients. Moreover, trans, E-1-crotonoyl-2,2,6-trimethylcyclohexane is very effective in improving the flavour of natural extracts such as raspberry concentrates and other berry or stone fruit concentrates. As little as 0.004% of trans, E-1-crotonoyl-2,2,6-trimethylcyclohexane in a natural raspberry concentrate dramatically improves the raspberry flavour. This level corresponds with 0.1 ppm of trans, E-1-crotonoyl-2,2,6-trimethylcyclohexane in the finished product. The level of trans, E-1-crotonoyl-2,2,6-trimethylcyclohexane in finished products like beverages, icecream, candy, dessert mixes etc. is thus usually below 1 ppm and sometimes as low as 0.1 ppb. This may be higher for chewing gum.

The organoleptic quality of cis, E-1-crotonoyl-2,2,6-trimethylcyclohexane is quite different from that of the trans, E-isomer. The effect is far less fruity, while the earthy-minty aspect becomes dominating. The cis, E isomer is of little value for use in flavouring compositions. The two Z isomers were found to be of far less interest for either perfume or flavouring purposes.

EXAMPLE 1

Preparation of cis-1-acetyl-2,2,6-trimethylcyclohexane (VI)

464 g 1-acetyl-2,2,6-trimethyl-4-cyclohexene (V, prepared according to K. S. Ayyar Chem.Comm. 1973, 161) (2.8 moles) in 800 ml of ethanol and 3 g 10% palladium on charcoal are hydrogenated in an autoclave under a pressure of 50 atm and at 50° C. After the uptake ceases, the reaction mixture is filtered and concentrated by distillation under reduced pressure. The product cis-1-acetyl-2,2,6-trimethylcyclohexane (VI, containing about 10% of the trans isomer) is collected at 83°–88° C/12 mm; yield 420 g (90%).

EXAMPLE 2

Preparation of cis-1-(2,2,6-trimethylcyclohexyl)-3-butanol-one-1 (VII)

To 750 ml of an etheral solution of ethylmagnesium bromide (prepared from 302 g (2.7 moles) of ethyl bromide and 58,7 g (2.4 moles) magnesium turnings in 550 ml of ether) is added with cooling and stirring a solution of 238 g (2.2 moles) of freshly distilled dry N-methylaniline in 700 ml of dry benzene ($N_2$ atmosphere). To the above freshly prepared solution of N-methylanilinomagnesium bromide is added during 25–30 minutes a solution of 370 g (2.2 moles) of 1-acetyl-2,2,6-trimethyl cyclohexane (VI) in 370 ml of dry benzene while keeping the temperature at 15° C. After the addition of the ketone, the solution is allowed to stand for 30 minutes. A solution of 145.5 g (3.3 moles) of freshly distilled acetaldehyde in 150 ml of dry benzene is then added during 45 minutes, keeping the temperature at −13° to −10° C. After the addition of the aldehyde, the solution is allowed to stand for 90 minutes at the same temperature. 2000 ml of 3N hydrochloric acid is then added with stirring and cooling. The organic layer is separated and washed 6 times with 1000 ml 3N hydrochloric acid (to remove the N-methylaniline) and finally with 500 ml of water, 500 ml of sodium bicarbonate solution, and then water. The combined organic layers are dried over, anhydrous sodium sulfate and the solvents are removed by distillation at reduced pressure. The residue is distilled through a short Vigreux column. The product, cis-1-(2,2,6-trimethylcyclohexyl)-3-butanolone-1 (containing about 10% of the trans isomer) is collected at 98°–104° C/1 mm; yield 320 g (70%).

EXAMPLE 3

Preparation of cis, E-1-crotonoyl-2,2,6-trimethylcyclohexane (III)

A solution of 320 g (1.5 moles) of the ketol prepared in Example 2 in 1000 ml of benzene containing 2 g p-toluene-sulphonic acid is heated in an apparatus for azeotropical water separation (Dean-Stark) till no more water separates. The reaction mixture is washed with a solution of sodium bicarbonate till neutral reaction and dried over anhydrous sodium sulfate. The solvent is removed by distillation at reduced pressure and the residue is distilled through a short Vigreux column. The product, cis, E-1-crotonoyl-2,2,6-trimethyl-cyclohexane (III, contains about 10% of the trans isomer) is collected at 76° C/1 mm; yield 273 g (94%). Recrystallization from pentane gives cis, E-1-crotonoyl-2,2,6-trimethylcyclohexane in high purity (m.p. 27°–28° C).

EXAMPLE 4

Conversion of a mixture of predominantly cis-1-acetyl-2,2,6-trimethyl cyclohexane (VI) into a mixture of predominantly the trans isomer (VIII)

A mixture of 185 g mostly cis-1-acetyl-2,2,6-trimethylcyclohexane (as prepared in example 1) and 550 g of polyphosphoric acid is heated at 150° C for about one hour. The reaction mixture is cooled to below 100° C, whereafter crushed ice is added. The mixture is extracted with benzene. The obtained extract is washed subsequently with water, a solution of sodium bicarbonate and again water, and dried over anhydrous sodium sulfate. The solvent is removed by distillation at reduced pressure and the residue is distilled through a short Vigreux column. The product, predominantly trans-1-acetyl-2,2,6-trimethylcyclohexane, is colleced at 85°–88° C/10 mm; yield 155 g (84%).

EXAMPLE 5

Preparation of trans, 1-(2,2,6-trimethylcyclohexyl)-3-butanolone-1 (IX)

By repeating of the procedure described in example 2 but replacing cis-1-acetyl-2,2,6-trimethylcyclohexane (VI) by the trans isomer VIII (as prepared in example 4) there is obtained 67% of a mixture of the ketols IX and VII, b.p. 105°–110° C/1 mm.

EXAMPLE 6

Preparation of trans, E-1-crotonoyl-2,2,6-trimethylcyclohexane (I)

By repeating the procedure described in Example 3 but now starting from 130 g (0.61 mole) of the ketol mixture prepared in Example 5, there is obtained 99 g (84%) of a 87:13 mixture of trans, E (I) and cis, E-1-crotonoyl-2,2,6-trimethyl-cyclohexane (III), b.p. 92°–94° C/12 mm. Recrystallization from pentane gives trans, E-1-crotonoyl-2,2,6-trimethyl-cyclohexane in high purity, m.p. 8°–9° C.

EXAMPLE 7

Epoxidation of trans-dihydroionone (X)

130 ml of a 30% aqueous hydrogen peroxide solution (1.1.moles) are dropped with stirring into a solution of 97 g (0.5 mole) trans-dihydroionone and 40 ml 4N sodium hydroxide solution in 500 ml of methanol. The reaction mixture is kept at 40° C during 14 hours and then diluted with 2.5 liters of water, saturated with sodium chloride and extracted three times with 200 ml of methylene chloride. The combined organic layers are washed with water and dried over anhydrous sodium sulfate.

The solvent is removed by distillation at atmospheric pressure and the residue is distilled through a short Vigreux column. The product, trans-dihydroionone epoxide is collected at 90°-92° C/1 mm; yield 82 g (80%).

EXAMPLE 8

Preparation of trans, E and trans, Z-1-(2,2,6-trimethylcyclohexyl)-2-butenol-2 (XII and XIII)

In a 1-L three-necked flask fitted with a mechanical stirrer, a thermometer and a nitrogen inlet tube is placed a solution of 75 g (0.36 moles) trans-dihydroionone epoxide (XI) in 360 ml of dry methanol. Dry nitrogen is let in and within 10 minutes 53,5 g (1.0 mole) 99% hydrazine hydrate is added at a temperature of about 15° C while cooling with ice water.

Acetic acid (4.3 ml) is then added and nitrogen is evolved. The temperature is kept around 15° C for 4 hours after which the nitrogen evolution subsides. The reaction mixture is diluted with 1 liter of water, then saturated with sodium chloride and extracted with ether. The combined organic layers are subsequently washed with water, a solution of sodium bicarbonate till neutral reaction, and again with water. The etheral solution is dried over anhydrous sodium sulfate and the solvent removed by distillation at atmospheric pressure. The residue is distilled through a short Vigreux column. The product, a mixture of trans, E and trans, Z-1-(2,2,6-trimethyl-cyclohexyl)-2-butenol-1 (XII and XIII) is collected at 80°-86° C/0,3 mm; yield 38 g (55%).

EXAMPLE 9

Oxidation of trans, E and trans, Z-1-(2,2,6-trimethylcyclohexyl)-2-butenol-1 (XII and XIII)

A solution of 7 g of the mixture of alcohols (obtained as described in Example 8), in 350 ml of dry pentane is stirred with 70 g of activated manganese dioxide during 35 hours. The course of the reaction is followed by gas chromatographic analysis. The inorganic material is removed by filtration and the solvent by distillation at atmospheric pressure. The product, 1-crotonoyl-2,2,6-trimethylcyclohexane is collected by distillation at 74° C/1 mm; yield 3.5 g (50%). The two components were separated by preparative vapour phase chromatography and found (from their IR and NMR spectra) to be the trans, Z (II) and trans, E (I) forms (30:70). On standing II isomerizes to I.

EXAMPLE 10

Epoxidation of α-ionone a solution of 150 g (0.78 mole) of α-ionone and 80 ml of 6N sodium hydroxide solution in 865 ml of methanol is brought to 35° C. 282 ml of a 35% aqueous hydrogen peroxide solution (2.9 moles) are added with stirring during 45 minutes. The reaction mixture is kept at 35°-40° C during 4 hours and then concentrated to 500 ml. The residue is diluted with 300 ml of water, saturated with sodium chloride and extracted three times with 200 ml of chloroform. The combined organic layers are washed with water and dried over anhydrous sodium sulfate. The solvent is removed by distillation at reduced pressure and the residue is distilled through a short Vigreux column. The product, α-ionone epoxide (XIV), is collected at 98°-102° C/1 mm; yield 114 g (70%).

EXAMPLE 11

Hydrogenation of α-ionone epoxide (XIV)

A solution of 130 g α-ionone epoxide (XIV) (0.62 mole) in 300 ml of glacial acetic acid is hydrogenated in a Parr hydrogenation apparatus with 1 g platinum oxide as a catalyst under a pressure of 50 p.s.i. till the uptake ceases. The small amount of dihydroionol epoxide which is also formed, is reoxidized by adding enough chromic acid solution in water at 25°-35° C to create a persistent orange-red colour for one hour. The reaction mixture is diluted with 1 liter of water, then extracted three times with pentane. The combined organic layers are washed with water and a solution of sodium bicarbonate till neutral reaction and dried over anhydrous sodium sulfate. The solvent is removed by distillation at reduced pressure and the residue is distilled through a short Vigreux column. The product, consisting of cis (90%) (XV) and trans (10%) (XI) dihydroionone epoxide is collected at 96°-97° C/1 mm; yield 95 g (70%).

EXAMPLE 12

Preparation of 1-(2,2,6-trimethylcyclohexyl)-2-butenol-1

The same procedure as is described in Example 8 is applied to 90 g (0,42 mole) of the mixture of cis- and trans-dihydroionone epoxide, as obtained in Example 11. The product, a mixture of all four stereoisomers of 1-(2,2,6-trimethylcyclohexyl)-2-butenol-1 is collected at 92°-96° C/1 mm; yield 33 g (40%).

EXAMPLE 13

Oxidation of the mixture of alcohols from example 12

The same procedure as is described in Example 9 is applied to 25 g (0,13 mole) of the mixture of alcohols obtained in Example 12. The product, a mixture of all four stereoisomers of 1-crotonoyl-2,2,6-trimethylcyclohexane (III:IV:I:II in a ratio of 60:27:9:4) is collected by distillation at 80°-90° C/1 mm; yield 13 g (50%). cis, Z (IV) is isolated from the foregoing mixture by preparative vapour phase chromatography.

EXAMPLE 14

Preparation of a raspberry flavouring composition. A raspberry flavouring composition was prepared by mixing together the following ingredients (parts by weight):

| Ingredient | Parts |
|---|---|
| α-terpineol | 10 |
| p-hydroxyfenylbutanone | 5 |
| Isoamyl acetate | 10 |
| Isobutyl acetate | 6 |
| α-Ionone | 10 |
| Buchu oil 10% in propylene glycol | 2 |

-continued

| | | |
|---|---|---|
| Dimethylsulfide 10% in propylene glycol | | 2 |
| Benzyl alcohol | | 25 |
| Propylene glycol | | 926 |
| | total | 996 |

Various test compositions were prepared as follows:

(a) A 10% propylene glycol solution, of trans,E-1-crotonoyl-2,2,6-trimethylcyclohexane (4 g) was added to 996 g of above-mentioned composition.

(b) A 10% propyleneglycol solution of cis,E-1-crotonoyl-2,2,6-trimethylcyclohexane (4 g) was added to 996 g of the above-mentioned composition.

(c) A 10% propylene glycol solution of E-β-damascenone (E. Demole et al., loc.cit.) (4 g) was added to 996 g of the above-mentioned composition.

(d) A 10% propylene glycol solution of E-β-damascone (E. Demole et al., loc.cit.) (4 g) was added to 996 g of the above mentioned composition.

A 'control' composition was prepared by adding 4 g of additional propylene glycol to 996 g of the above mixture.

The flavour effect of the control and test compositions thus obtained was compared by application in drinks prepared by adding 15 ml of concentrated sugar syrup (60%), 0.1 g of citric acid 50% in water, 85 ml water and 1 g of a 1% solution of the control and test composition.

Comparative tests by a test panel gave the following results.

The drink with the 'control' flavour composition possesses certain raspberry flavour characteristics, but not very pronounced or 'natural'.

The drink with flavour (a) was found to be tastewise a definite improvement over the control. A natural raspberry effect is the result. This shows that addition of a certain quantity (as indicated) of trans,E-1-crotonoyl-2,2,6-trimethylcyclohexane is a very desirable improvement.

The drink with flavour (b) still has a thin taste; no improvement over the control.

The drink with flavour (c) was found to be some improvement over the 'control' drink but the taste effect of E-β-damascenone is quite jammy and woody, which effect is less natural and desirable when compared with flavour (a).

The drink with flavour (d) was also found to possess a rather jammy and woody (ionone-like) taste. This type of taste is much less desirable than the taste of the drink with flavour a).

EXAMPLE 15

Preparation of a rhubarb flavouring composition

A rhubarb flavouring composition was prepared by mixing together the following ingredients (parts by weight):

| | | |
|---|---|---|
| Styrallyl acetate | | 40 |
| Dimethylbenzylcarbinyl butyrate | | 30 |
| Ethyl acetate | | 10 |
| Ethyl butyrate | | 5 |
| Lemon oil | | 15 |
| Benzyl alcohol | | 50 |
| Propylene glycol | | 846 |
| | total | 996 |

A 'control' composition was prepared by adding 4 g of additional propylene glycol to 996 g of the above mixture.

Test compositions were prepared as follows:

(a) A 10% solution (in propylene glycol) of trans,E-1-crotonoyl-2,2,6-trimethylcyclohexane (4 g) was added to 996 g of the basic composition.

(b) A 10% solution (in propylene glycol) of cis,E-1-crotonoyl-2,2,6-trimethylcyclohexane (4 g) was added to 996 g of the basic composition.

(c) A 10% solution (in propylene glycol) of E-β-damascenone (E. Demole et al., loc.cit.) (4 g) was added to 996 g of the basic composition.

(d) A 10% solution (in propylene glycol) of E-β-damascone (E. Demole et al., loc.cit.) added to 996 g of the above mentioned composition.

The flavour effect of the compositions thus obtained was compared by application in drinks prepared as mentioned in example 14. Comparative tests by a test panel gave the following results.

The drink with flavour (a) was found to possess a rhubarb-like taste with an effect of increased ripeness and sweetness, when compared with the taste of the 'control' drink.

The drink with flavour (b) was found to be slightly metallic in taste, and no improvement over the control.

The drink with flavour (c) had lost the characteristics of rhubarb, when compared with the control. The taste of the drink was found to be too sweet and woody to be characteristic rhubarb.

The same effect was found in the drink with flavour (d).

EXAMPLE 16

Flavouring of natural juices and concentrates

A red currant juice concentrate was mixed with 1 ppm of the compounds mentioned earlier, thus yielding the following products:

(a) Red currant juice concentrate with 1 ppm of trans,E-1-crotonoyl-2,2,6-trimethylcyclohexane.

(b) The same concentrate with 1 ppm of cis,E-1-crotonoyl-2,2,6-trimethylcyclohexane.

(c) The same concentrate with 1 ppm of E-β-damascenone (E. Demole et al., loc.cit.

(d) The same concentrate with 1 ppm E-β-damascone (E. Demole et al., loc.cit.).

The flavour of the concentrates *a, b, c, d* and a 'control' was compared by tasting drinks prepared by adding 15 ml of concentrated sugar syrup (60%), 0.1 g of citric acid 50% in water, 85 ml of water and 0.3 g of the juice concentrate. Comparative tests by a test panel gave the following results.

Concentrate (a) was found to possess a strongly increased very natural currant taste when compared with the 'control' drink.

Concentrate (b) was found to possess a much less natural currant taste.

Concentrate (c) was found to have a jammy-raspberry-like character which does not bring the product closer to natural red currant taste. The same is true for concentrate (d) but here the effect of raspberry similarity is even less pronounced.

We claim:

1. A fruit flavoring composition, for flavoring a food product, to which has been added trans, E-1-crotonoyl-2,2,6-trimethylcyclohexane in an amount which is effective to impart a fresh, fruity flavor to said flavoring composition.

2. A flavoring composition according to claim 1, wherein the effective amount of said trans, E-1-crotonoyl-2,2,6-trimethylcyclohexane varies from 0.001% to 1% by weight of the flavoring composition.

3. The flavoring composition of claim 1, wherein the flavoring composition is comprised of a raspberry flavoring composition.

4. The flavoring composition of claim 3, wherein the raspberry flavoring composition is further comprised of a-terpineol, p-hydroxyfenylbutanone, isoamyl acetate, isobutyl acetate, a-Ionone, buchu oil 10% in propylene glycol, dimethylsulfide 10% in propylene glycol, benzyl alcohol, and propylene glycol.

5. The flavoring composition of claim 1, wherein the flavoring composition is comprised of a rhubarb flavoring composition.

6. The flavoring composition of claim 5, wherein said rhubarb flavoring composition is comprised of styrallyl acetate, dimethylbenzylcarbinyl butyrate, ethyl acetate, ethyl butyrate, lemon oil, benzyl alcohol and propylene glycol.

7. The flavoring composition of claim 1, wherein the flavoring composition is comprised of a red currant juice concentrate.

8. A method of flavoring food comprising adding thereto, in an amount effective to impart a fresh, fruity flavor, trans, E-1-crotonoyl-2,2,6-trimethylcyclohexane.

* * * * *